US005713930A

United States Patent [19]

van der Veen et al.

[11] Patent Number: 5,713,930
[45] Date of Patent: Feb. 3, 1998

[54] DUAL CHAMBER PACING SYSTEM AND METHOD WITH CONTROL OF AV INTERVAL

[75] Inventors: Johannes S. van der Veen, Dieren; Geeske van Oort, Nieuwleusen, both of Netherlands

[73] Assignee: Vitatron Medical, B.V., Dieren, Netherlands

[21] Appl. No.: 744,576

[22] Filed: Nov. 6, 1996

[51] Int. Cl.[6] .................................................. A61N 1/365
[52] U.S. Cl. ......................................................... 607/25
[58] Field of Search ................................. 607/9, 25, 28

[56] References Cited

U.S. PATENT DOCUMENTS

| | | | |
|---|---|---|---|
| 4,428,378 | 1/1984 | Anderson et al. | |
| 4,527,568 | 7/1985 | Rickards | 607/25 |
| 4,665,919 | 5/1987 | Mensink et al. | |
| 4,972,834 | 11/1990 | Begemann et al. | 607/25 |
| 5,052,388 | 10/1991 | Sivula et al. | |
| 5,267,560 | 12/1993 | Cohen | 607/25 |
| 5,330,511 | 7/1994 | Boute | 607/25 |
| 5,334,220 | 8/1994 | Sholder | 607/9 |
| 5,534,016 | 7/1996 | Boute | 607/9 |

OTHER PUBLICATIONS

Boute, W. et al., "Morphology of Endocardial T-Waves of Fusion Beats," PACE, vol. 11, Nov. 1988, Part II, 1693–1697.

Primary Examiner—Marvin M. Lateef
Assistant Examiner—George R. Evanisko
Attorney, Agent, or Firm—Woodcock Washburn Kurtz Mackiewicz & Norris LLP

[57] ABSTRACT

A dual chamber pacemaker system and method is provided for adjusting AV delay to provide for an optimal AV setting for a selected pacing application. In the inventive system and method, the basis for determining the AV delay setting is to perform a ventricular fusion test, wherein variations in QT interval are monitored corresponding to variations in AV interval. Based upon the AV-QT data, the pacemaker can determine the ventricular fusion zone where the pacemaker AV interval is substantially the same as the intrinsic conduction interval, as well as the knee where AV intervals just shorter than the ventricular fusion zone result in full capture. The pacemaker selects a routine for adjusting AV interval depending upon a desired application, including the applications of adjusting AV interval for full capture and for treatment of a HOCM patient. There is also provided a routine for determining an appropriate AV hysteresis value for inhibiting ventricular pacing and allowing ventricular sensing as much as possible, for patients with intermittent AV block.

13 Claims, 8 Drawing Sheets

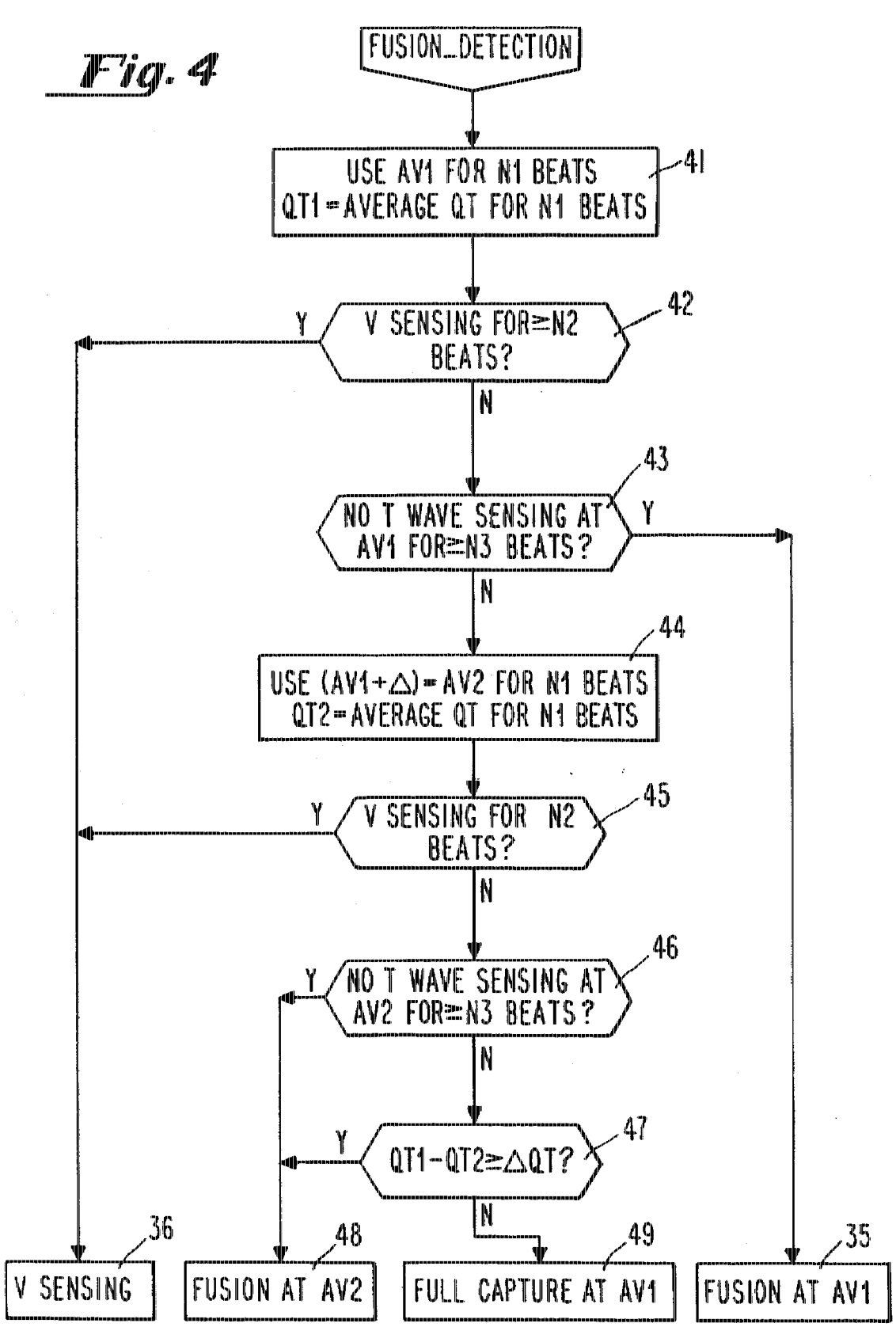

DUAL CHAMBER PACING SYSTEM AND METHOD WITH CONTROL OF AV INTERVAL

FIELD OF THE INVENTION

This invention relates to cardiac pacing systems and methods and, in particular, to dual chamber cardiac pacing systems and methods where the AV interval is adjusted to optimize synchronization of the ventricular pace pulse with a preceding atrial event.

BACKGROUND OF THE INVENTION

The value of dual chamber cardiac pacing and treatment has been recognized in the literature. Modern multiple-mode, dual-chamber cardiac pacemakers are designed to maintain AV synchrony for damaged or diseased hearts that are unable to do so on their own. For example, a DDD pacemaker system has lead connections to both the atrium and the ventricle; senses electrical signals in both chambers of the patient's heart; delivers atrial pacing stimuli in the absence of signals indicative of natural atrial contractions; and delivers ventricular pacing stimuli in the absence of signals indicative of natural ventricular contractions. Such a dual chamber pacemaker maintains the AV synchrony of the heart by delivering ventricular pace pulses at a controlled AV interval following each atrial event.

An important feature of the dual chamber pacemaker is to optimally set the AV interval, or the escape interval between either an atrial sense (AS) or atrial pace (AP), and the timing of a subsequent ventricular pace pulse (VP). For patients with intermittent AV conduction, or occasional AV block, it is desired to set AV delay to be just greater than the natural conduction interval, so that spontaneous beats are permitted. However, for patients with slow conduction, it is desired to deliver a VP at timeout of an AV interval which approximates the healthy conduction interval, or even slightly earlier to insure full capture by the VP. Another application where optimal adjustment of the AV interval is important is that of pacing patients suffering from hypertrophic obstructive cardiomyopathy (HOCM). Studies have indicated that patients suffering from HOCM may benefit from a specific mode of dual chamber pacing wherein a ventricular pace pulse is delivered in timed synchrony with the sensed or paced atrial alepolarization. Pacing the right ventricular apex just before spontaneous atrio-ventricular conduction activates the left ventricle is understood to alter the ventricular septal activation pattern. This reduces leftward motion of the septum, thereby reducing the LVOT obstruction and subaortic pressure gradient. Accordingly, for HOCM patients, it is desired to use the longest AV interval that produces full capture and avoids ventricular fusion.

For yet another group of patients with right bundle branch block, it is desired to adjust AV interval to approximate the ventricular fusion value, i.e., aim for ventricular fusion beats. It is thus seen that there is a need in a variety of applications for obtaining a measure of the patient's intrinsic AV conduction time (AVC) and adjusting the pacemaker AV interval accordingly. A general technique for doing this is to determine the AV interval that corresponds to ventricular fusion, or the point where a delivered pace pulse substantially coincides with an intrinsic ventricular beat. See, for example, U.S. Pat. No. 5,534,016, which discloses a pacing system for detecting ventricular fusion as a technique for adjustment of the AV delay as therapy for HOCM. In that patent, the amplitude of the T-wave is monitored as the AV interval is varied, to determine the AV interval which corresponds to ventricular fusion. The pacing literature contains other examples of varying AV interval to find an interval which achieves capture. However, our studies have indicated that ventricular fusion is not detected as a precise point, but rather is found to be zone of AV intervals extending from shorter values of AV delay where there is moderately good capture, to longer values where there is no capture because of the intervening intrinsic heartbeat, with the zone in between being characterized by changes in the QRS and T-waves. Indeed, within the ventricular fusion zone it becomes difficult if not impossible to sense the T-wave. What is thus indicated is the ability to determine the boundaries of the ventricular fusion zone, particularly the longest AV interval at which full capture is achieved, and adapt AV interval for each application as a function of the ventricular fusion zone boundaries.

SUMMARY OF THE INVENTION

This invention provides a pacing system and method which determines the effective ventricular fusion zone by monitoring variations in QT interval corresponding to changes in AV interval. For patients with some degree of AV conduction, the pacemaker of this invention provides for determining the ventricular fusion zone and the boundary of full ventricular capture, by monitoring the relationship between QT interval and AV delay. As used herein, QT refers to the time interval between a delivered ventricular stimulus and resulting T-wave. The pacemaker of this invention provides for adjustment of the AV delay through a test range for determining the relationship between QT interval and the ventricular fusion zone. The test range has an AV upper or high limit above the ventricular fusion zone, where intrinsic QRS signals occur before delivery of a pace pulse; and a lower limit below the zone, where there is complete ventricular capture following delivery of a VP. Variation of AV through this test range is accompanied by a determination of the corresponding QT interval for each value of AV delay. In shortening AV interval from a value greater than the ventricular fusion zone to a value less than the ventricular fusion zone, QT is found to increase to a point of full capture at the top, or knee of the ventricular fusion zone. Further, in pacing through the ventricular fusion zone, it is found that the T-wave amplitude drops such that it is not always identifiable, further defining the ventricular fusion zone. With the thus obtained QT information, AV can be accurately set in accordance with the desired application, i.e., either greater than the ventricular fusion zone, shorter than the ventricular fusion zone, or substantially in the ventricular fusion zone.

More specifically, there is provided a ventricular fusion detection scheme where the pacemaker monitors the AV and QT relationship at two AV values, e.g., the current value (AV1) and an incrementally longer value (AV2). This test enables determination of whether the current AV value is near the ventricular fusion zone knee, or in the ventricular fusion zone. Following this determination, the pacemaker can respond according to a selected application. Thus, where full capture is desired, the pacemaker sets AV to provide full capture, and performs a ventricular fusion detection test to accurately determine the AV-QT knee, so that the maximum AV limit for full capture is known. For a HOCM application, AV is set to the longest value that is just short of the ventricular fusion zone. In yet another application, the pacemaker scans AV values to determine a proper AV hysteresis setting to be used following VS events, which optimizes natural ventricular beats for patients with intermittent AV block.

BRIEF DESCRIPTION OF THE DRAWINGS

FIG. 4 is a flow diagram of a ventricular fusion detection test according to this invention.

DETAILED DESCRIPTION OF THE PREFERRED EMBODIMENTS

Figure 1:
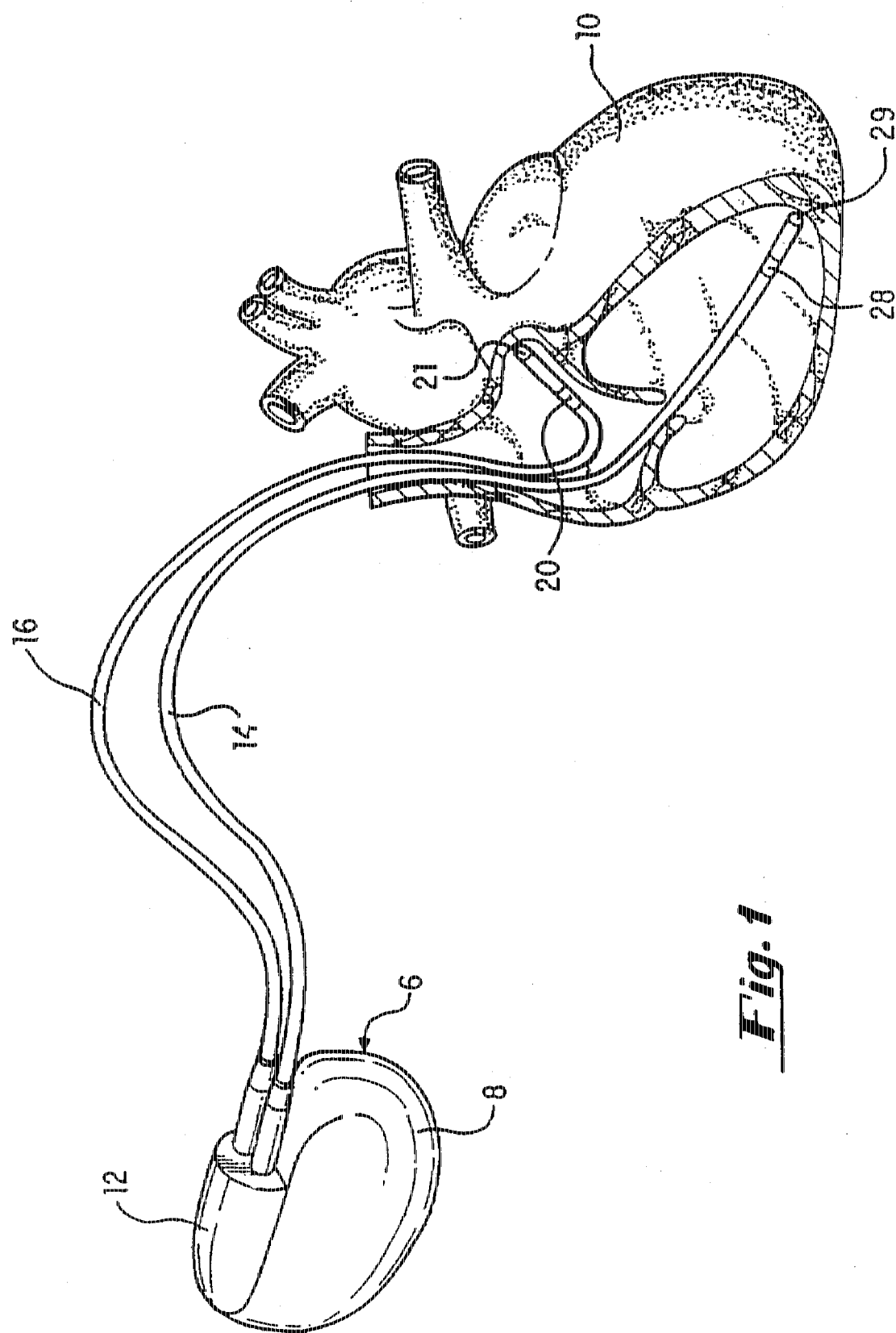
FIG. 1 is a perspective representation of the pacemaker system of this invention showing an implantable pacemaker connected to a patient's heart.

FIG. 1 illustrates the external configuration of a dual chamber pacemaker 6, which is provided with a hermetically sealed enclosure 8, typically fabricated of biocompatible metal such as titanium. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrode 20 and 21 and the housing 8 of the pacemaker 6.

Similarly, lead 14 represents a ventricular bipolar pacing lead, carrying two electrodes 28 and 29. As discussed above in conjunction with atrial lead 16, electrodes 28 and 29 are used to sense and pace the ventricle. Ventricular pacing may be accomplished between electrodes 29 and 28 or between electrode 29 and the conductive housing 8 of pacemaker 6. Sensing of ventricular signals, including depolarizations (QRS-waves) and repolarizations (T-waves) may be accomplished between electrodes 29 and 28 or between either of electrodes 29 and 28 and the housing 8 of the pacemaker 6.

As discussed in the present application, the preferred embodiments of the pacemaker 6 operate in a DDD or DDDR pacing mode, wherein pacing pulses are delivered to both atrium and ventricle and wherein atrial and ventricular depolarizations are both effective to inhibit delivery of the next scheduled pacing pulse in the chamber in which they are detected. DDDR may be indicated for patients that have drug-induced chronotropic incompetence. While the present invention is believed optimally practiced in a pacemaker operating in DDD or DDDR pacing mode, in some patients there may also be a benefit to operating the device in DDI, VDD or DVI mode, which provides ventricular pacing pulses synchronized only to sensed atrial depolarizations or only to delivered atrial pacing pulses, respectively, depending upon the specific underlying heart condition of the patient. However, DDD or DDDR mode is expected to be the mode most widely used to practice the present invention.

Figure 2:
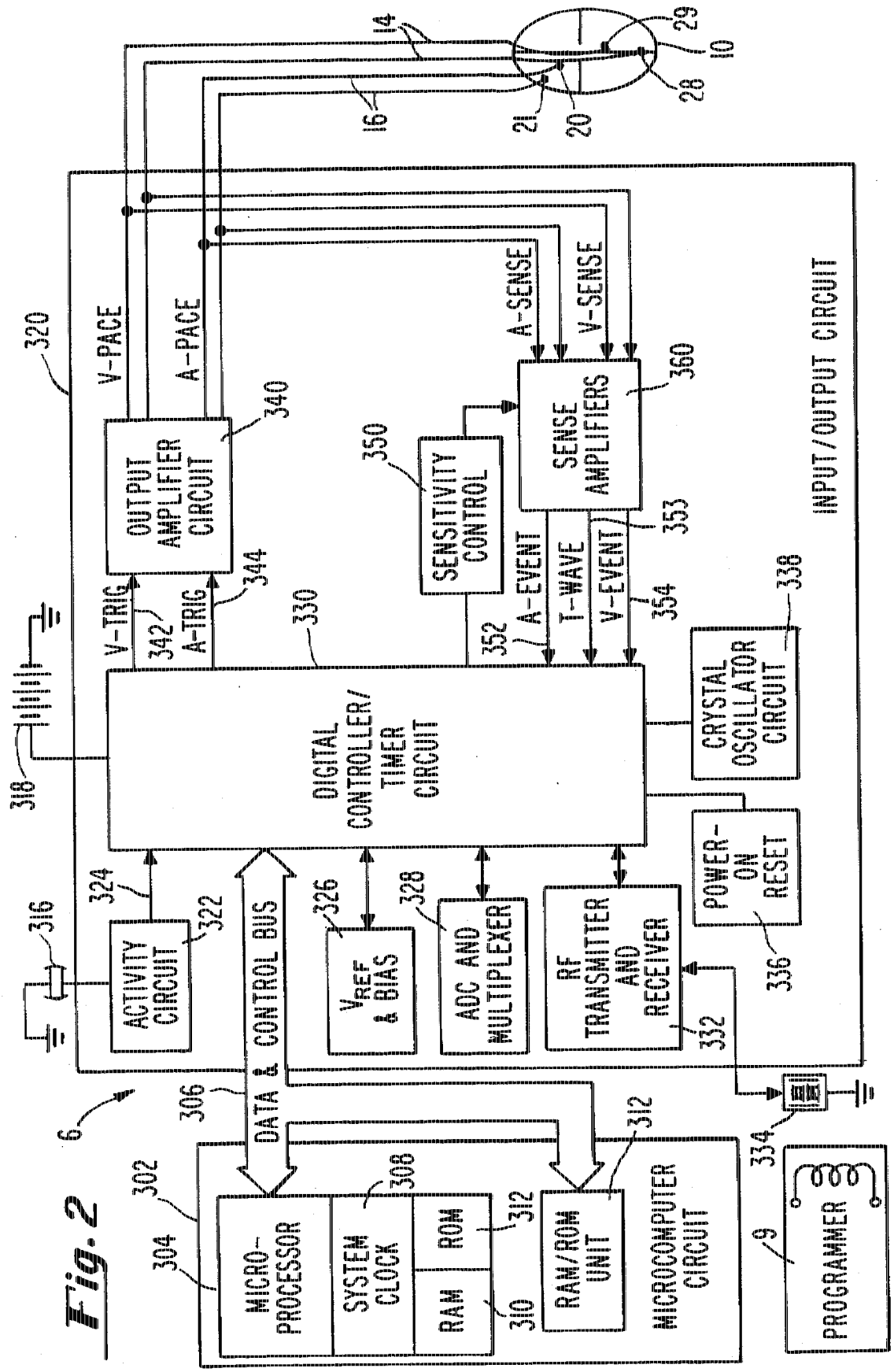
FIG. 2 is a block diagram of the primary functional components of the pacemaker system and method of this invention.

FIG. 2 is a block functional diagram of the pacemaker illustrated in FIG. 1, as connected to a human heart 10. The circuitry illustrated is all located within the conductive housing or can 8 of the pacemaker, as illustrated in FIG. 1, and the bipolar leads 14 and 16 are illustrated schematically as coupled directly to the circuit. However, of course, in the actual device they would be coupled by means of removable electrical connectors inserted in the connector block 12, as illustrated in FIG. 1.

The pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14, as well as an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16 as well. The ventricular sense amplifier provides for separate detection and identification of QRS-wave and T-wave signals, in a known manner. The output circuit 340 and sense amplifier circuit 360 may contain pulse generators and sense amplifiers corresponding to any of those presently employed in commercially marketed cardiac pacemakers. Control of timing and other functions within the pacemaker circuit is provided by digital controller/timer circuit 300, which includes a set of timers and associated logic. Digital controller/timer circuit 330 defines the basic pacing interval of the device, which may take the form of an A-A escape interval initiated on atrial sensing or pacing and triggering atrial pacing at the expiration thereof, or may take the form of a V-V escape interval, initiated on ventricular sensing or pacing and triggering ventricular pulse pacing at the expiration thereof. Digital controller/timer circuit 330 similarly defines the A-V escape interval, $AV_{esc}$, discussed in detail below. The specific values of the intervals defined are controlled by the microcomputer circuit 302 by means of data and control bus 306. Sensed atrial depolarizations are communicated to the digital controller/timer circuit 330 on A event line 352; ventricular depolarizations (QRS-waves) are communicated to the digital controller/timer circuit 330 on V event line 354; and ventricular repolarizations (T-waves) are connected to circuit 330 on T-wave line 353. In order to trigger generation of a ventricular pacing pulse, digital controller/timer circuit 330 generates a trigger signal on V trig line 342. Similarly, in order to trigger an atrial pacing pulse, digital controller/timer circuit 330 generates a trigger pulse on a trig line 344.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/ timer circuit 330 will also define an atrial refractory period during which atrial sensing is disabled, this refractory period extending from the beginning of the A-V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/ timer circuit 330 also controls sensitivity settings of the sense amplifiers 360 by means of sensitivity control 350. This sensitivity control may be utilized to distinguish QRS-waves and T-waves. See U.S. Pat. No. 4,665,919, incorporated herein by reference.

In the embodiment illustrated in FIG. 2, the pacemaker is provided with a piezo electric sensor 316 which is intended to monitor patient activity, in order to allow provision of rate responsive pacing, such that the defined pacing rate (A-A escape interval or V-V escape interval) increases with increased demand for oxygenated blood. Sensor 316 generates electrical signals in response to sensed physical activity which are processed by activity circuit 322 and provided to digital controller/timer circuit 330. Activity circuit 332 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Transmission to and from the external programmer 9 illustrated in FIG. 2 is accomplished by means of antenna 334 and associated RF transmitter and receiver 322, which serves both to demodulate received downlink telemetry and to transmit uplink telemetry. Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers.

Microcomputer circuit 302 controls the operational functions of digital controller/timer 330, specifying which timing intervals are employed, and controlling the duration of the various timing intervals, via data and control bus 306. Microcomputer circuit 302 contains a microprocessor 304 and associated system clock 308 and on processor RAM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every cycle or every two seconds, may be provided in order to allow the microprocessor to analyze the sensor data and update the basic rate interval (A-A or V-V) of the device. In addition, in a preferred embodiment of the invention, the microprocessor 304 may also serve to define variable A-V escape intervals and atrial and ventricular refractory periods which may also decrease in duration along with decreases in duration of the basic rate interval. Specifically, the microprocessor is used to carry out the routines illustrated in FIGS. 4–7.

The illustrated circuitry of FIG. 2 is merely exemplary, and corresponds to the general functional organization of most microprocessor controlled cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microprocessor circuit 302. However, the present invention many also be usefully practiced by means of a full custom integrated circuit, or any combination of hardware and software.

Figure 3A:
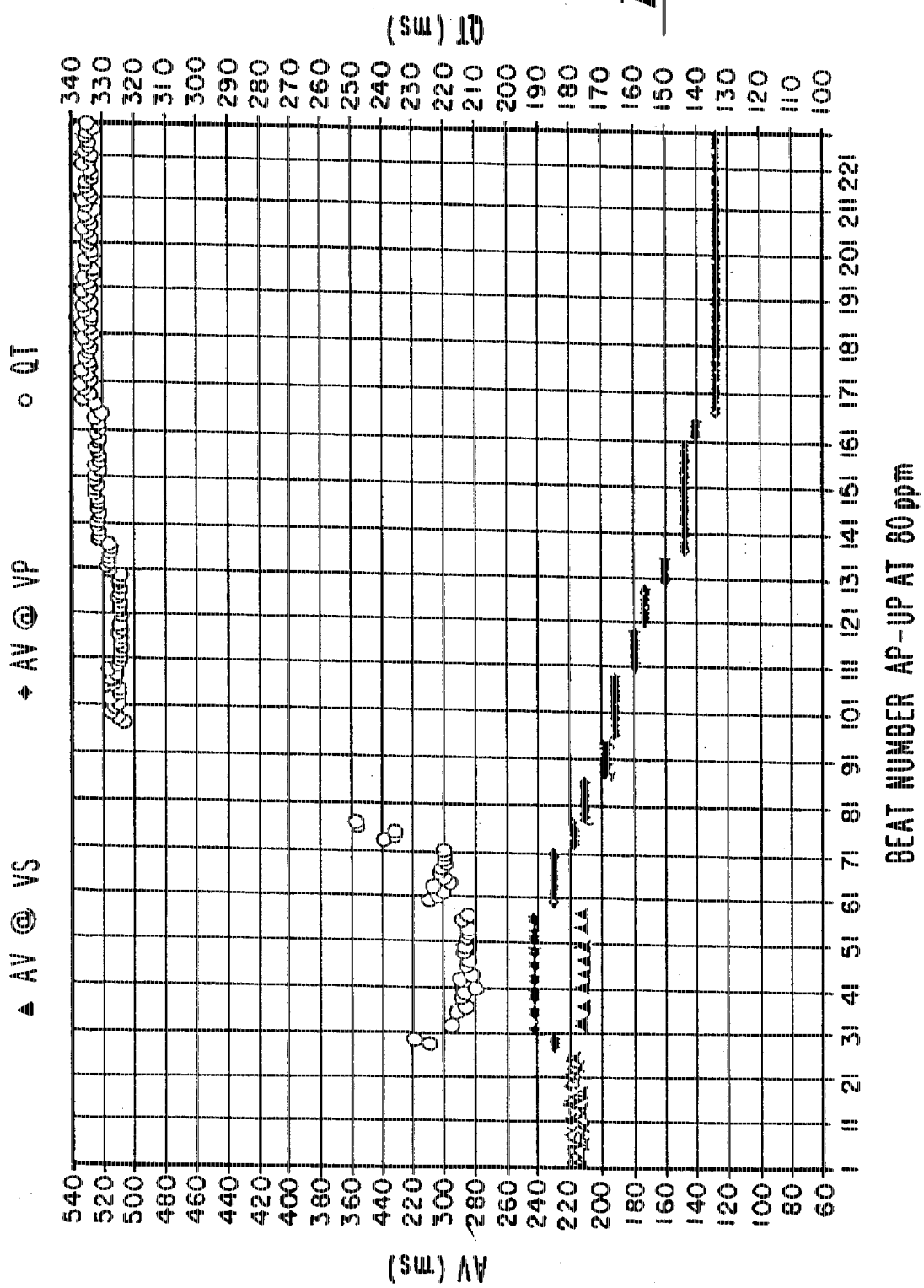
FIG. 3A is a graph representing variations in QT as a function of AV, for a patient with some form of AV conduction and having an implanted dual chamber pacemaker.

Referring now to FIG. 3A, there is shown a chart of data obtained with a dual chamber pacemaker implanted in a patient with some AV intrinsic conduction. It is seen that for low values of AV, starting at AV intervals between about 130–140 ms, there is consistent capture due to the delivered VP, while QT is substantially constant at around 330 ms. As AV interval is increased in steps, there is a slight decrease in QT, i.e., QT is in the area of 320 –330 ms for AV intervals up to around 200 ms. However, for AV in the range of about 200 –215, the T-wave cannot be measured, which is a further indication of ventricular fusion. As AV is increased from 220 up to about 230, only a few T-waves can be measured, but these indicate a substantial drop in QT interval. At an AV interval of about 230, QT is measured at about 220 ms. For AV at 240 ms, some of the ventricular beam result from pace pulses and some are spontaneous; QT interval following a VP has dropped to about 210 ms. For higher values of AV there is no pacing, and all ventricular heartbeats are natural. From this data, it is seen that there is a ventricular fusion zone for AV values that starts at about 150 ms, the center of the zone being in the range of about 200 –215 ms; and the knee for effective full capture due to a delivered pace pulse is around 140 –150 ms. As used in this application, the term "knee" refers to the AV delay at about which QT starts to decrease as AV is increasing.

Figure 3B:
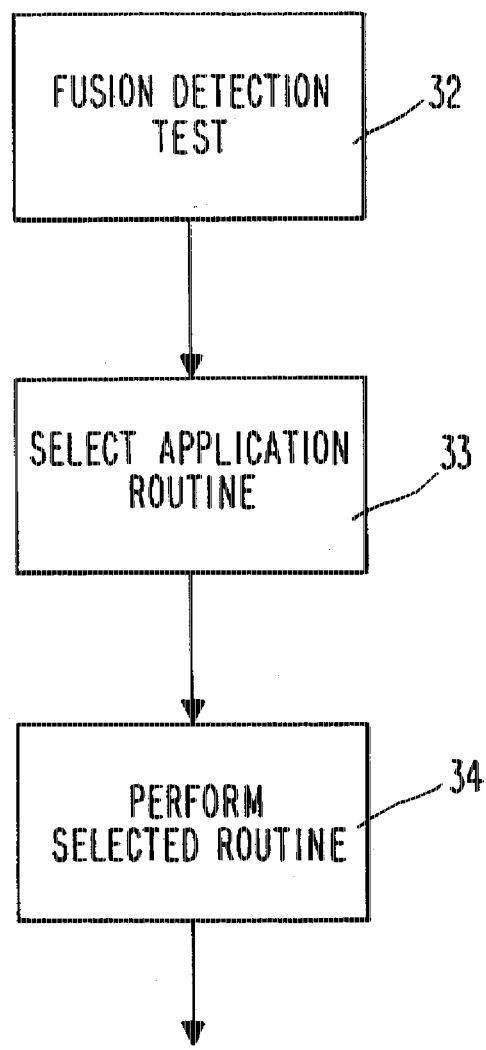
FIG. 3B is a flow diagram representing the method of performing a ventricular fusion detection test, and then performing a routine corresponding to a selected application.

With the information represented in FIG. 3A, the pacemaker of this invention can adjust AV interval in accord with the patient situation. Referring to FIG. 3B, there is shown a simplified diagram for utilizing the results of a ventricular fusion detection test as illustrated at block 32. The test can be a full test to obtain data as seen in FIG. 3A, or a more compact test to determine, from AV-QT data, where the present AV interval is with respect to the AV-QT knee, the start if the ventricular fusion zone. Following the test, the pacemaker selects an application routine, as shown at 33. This selection is preferably made in response to a command programmed for the patient, e.g., adjust AV for full capture, for sensing, for HOCM, etc. Based on this selection, the routine is performed as indicated at 34. Exemplary routines are set forth in FIGS. 5–7, as discussed below.

Referring now to FIG. 4, there is shown a flow diagram of steps taken in a "fusion detection" routine for determining where AV interval less relative to full capture or fusion. The basic technique is to compare QT intervals to different AV intervals which are separated by a predetermined increment, ΔAV. Of course, a precondition is that T-wave sensing is reliable, meaning that the sensitivity of the T-wave amplifier must be set properly. Generally, a T-wave sensitivity of 0.5 mV provides reliable T-wave sensing. Of course, as discussed above, for most patients it is expected that T-wave sensing will disappear for ventricular fusion situations. This absence of T-wave sensing is used by this invention as a means for locating the ventricular fusion zone.

Referring specifically to FIG. 4, at step 41 the current AV delay value of AV1 is used for N1 beats, during which N1 beats QT interval is recorded and averaged. Also, during the N1 beats, a count is made of the number of beats for which no T-wave is sensed. At step 42, it is determined whether there has been V sensing for more than N2 beats, where N2 is a predetermined fraction of N1. If yes, the routine branches to 36, and determines V sensing. At step 43, it is determined whether, for AV1, there has been a lack of T-wave sensing for greater than N3 beats, where N3 is another predetermined fraction of N1. If yes, this strongly indicates that AV1 is within the ventricular fusion zone, and the routine branches to block 35 and records data indicating ventricular fusion at AV1. If the answer at 43 is no, the routine proceeds to block 44, and sets a new value of AV, AV2=AV1+$\Delta$. The value of $\Delta$ is selected to be relatively small, so that for AV1 near the fusion knee, AV2 might be around the knee or into the fusion zone. The pacemaker operates again for N1 beats, at an AV delay of AV2. QT2, the average QT corresponding to AV2, is determined, and a count is made of the number of events where there was no T-wave sensing. At 45, it is again determined whether there has been V sensing for more than N2 beats. If no, at 46, it is determined whether there is an absence of T-wave sensing at AV2 for more than N3 beats. If yes, the routine branches to block 48, and records an indication of having found ventricular fusion at AV2. If the answer at 46 is no, the routine goes to block 47, and determines whether the QT1 average exceeds QT2 average by >$\Delta$QT. If yes, this indicates that AV2 is down the AV/QT slope from the knee, which indicates ventricular fusion, and at block 48 the determination of ventricular fusion at AV2 is made. However, if the comparison at 47 is no, this confirms that AV2 is still shorter than the edge of the ventricular fusion zone, and at 49 a determination is made that there is full capture at AV1.

Figure 5:
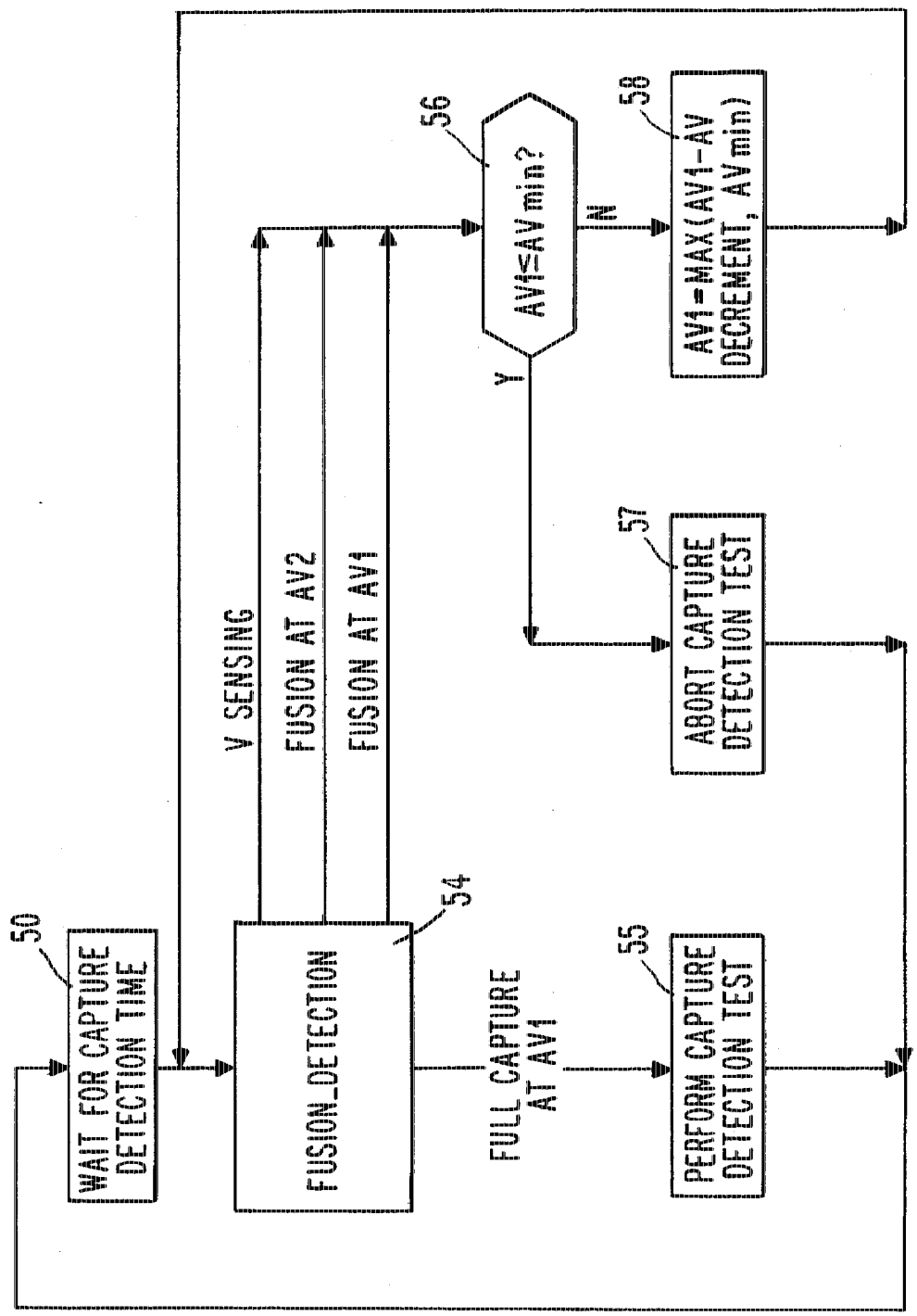
FIG. 5 is a flow diagram of a routine for performing a capture detection test based on a ventricular fusion detection test.

Referring now to FIG. 5, there is shown a flow diagram of a routine for adapting AV delay to provide for full capture, in those applications where it is desired to override any intrinsic conduction and pace as much as possible. At 50, a determination is made as to when it is time for a capture detection test, i.e., a test to automatically determine the pacing threshold, in accordance with a well known test procedure. For example, this test may be performed daily, or at any other predetermined interval. When the time has come, the pacemaker goes to step 54 and performs the fusion detection test, described in FIG. 4. Following the fusion detection test, it is determined whether full capture was found at AV1. If yes, the routine proceeds to 55 and performs a capture detection test. If, at 54, there is not full capture at AV1, this means either V sensing, fusion at AV1 or fusion at AV2. In any of these cases, it is desired to decrease AV, to see if capture can be obtained. After comparing AV1 to a predetermined $AV_{MIN}$ at 56, at 58 AV1 is set to the greater of AV1--AV decrement or $AV_{MIN}$, and the routine loops back to repeat the fusion detection. In this manner, AV1 is decremented to (1) where there is full capture and a capture test is performed at 55, or (2) where AV1 has been decremented to $AV_{MIN}$ or less, as determined at block 56. In this second case, the capture detection test is aborted, since it has already been determined that AV cannot be set low enough to achieve full capture.

Figure 6:
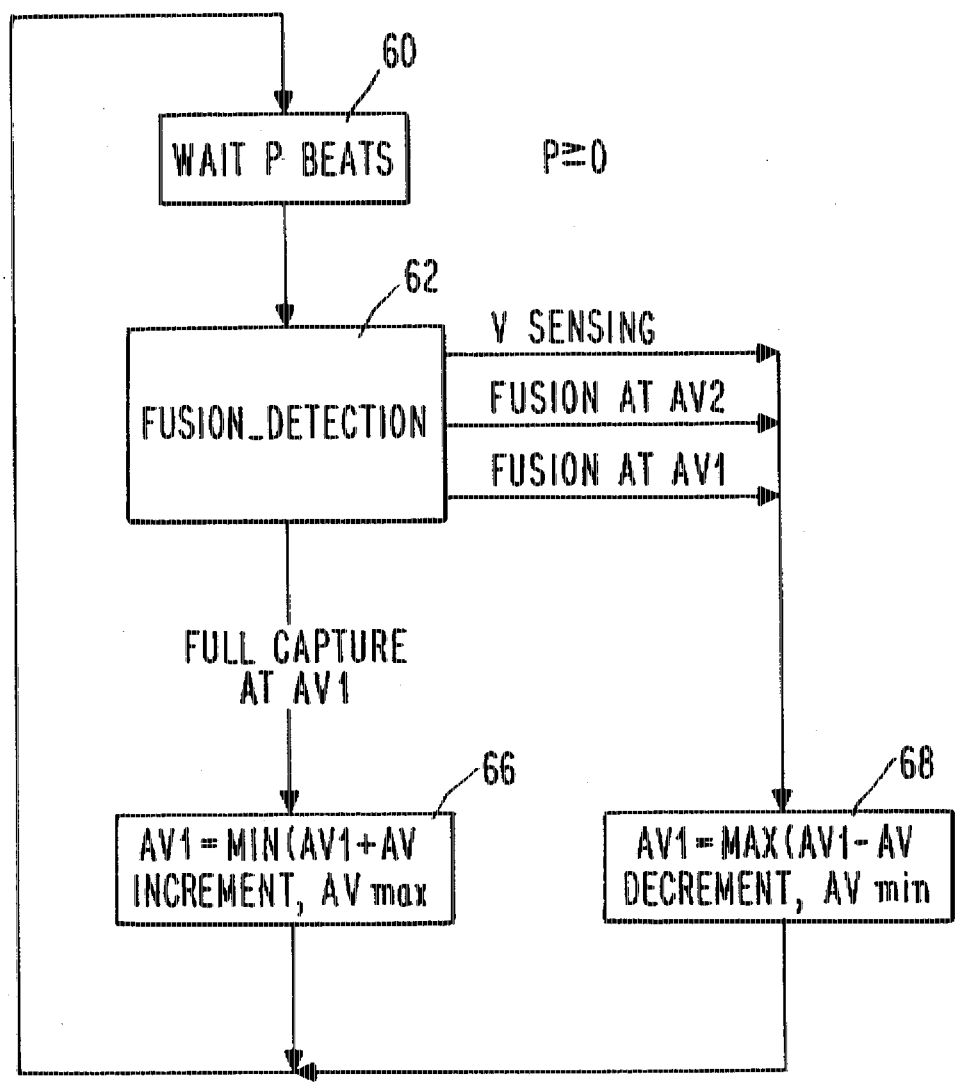
FIG. 6 is a flow diagram for adjusting AV for a HOCM application, based on a function detection test.

Referring now to FIG. 6, there is shown a simplified block diagram for adjusting AV delay to provide for optimum full capture for HOCM patients. As has been discussed above, for the HOCM application it is desired to pace synchronously with the longest possible AV interval short of the ventricular fusion zone. At block 60, the pacemaker waits for a predetermined number of beats, indicated as P, to provide a stable situation. Following this, at 62, the fusion detection test is performed, as shown in FIG. 4. This test determines whether there has been full capture at the present AV delay, AV1. If so, the routine goes to 66 and determines the value of AV1+AV increment. AV1 is then set to the minimum of the incremented value or $AV_{MAX}$. If, at 62, full capture has not been found at AV1, it is then desired to shorten the AV delay. The routine branches to block 68 and determines the value of AV13--AV decrement. AV1 is then set at the maximum of this value or $AV_{MIN}$.

Figure 7:
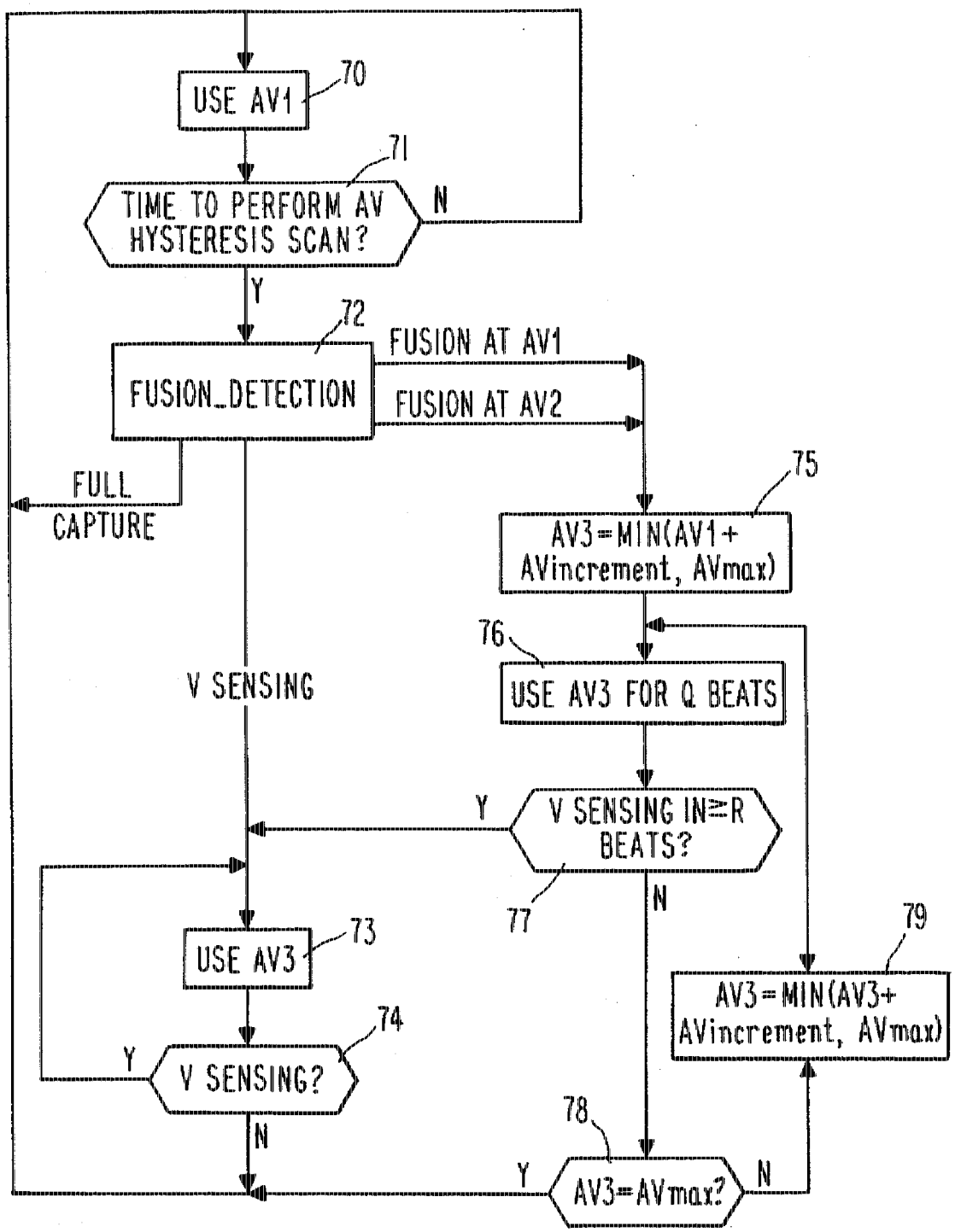
FIG. 7 is a flow diagram for adjusting the pacemaker AV hysteresis value, based on a ventricular fusion detection test.

Referring now to FIG. 7, there is shown a block diagram of a simplified routine for adjusting the AV hysteresis value for a pacemaker which utilizes AV hysteresis. As is known in the pacing art, AV hysteresis is a longer value of AV which is utilized after a VS, the regular shorter value being utilized after a preceding VP. As illustrated at 70, the routine starts with AV=AV1, the current value. At 71, it is determined whether it is time to perform a hysteresis scan, i.e., look for a proper AV hysteresis value (AV3). If yes, the fusion detection is performed at 72. If there is full capture, the routine returns to 70, and continues to use AV1 for pacing. If, at 72, V sensing is found, the routine goes to 73 and sets AV=AV3, the hysteresis value. As long as V sensing is found at 74, the AV3 value is used, but if a VP is found, the routine exits back to 70 and uses AV1. Returning to block 72, for a finding of ventricular fusion at AV1 or AV2, a hysteresis value of AV3 is set at 75, as the larger of (AV1+AV increment), or $AV_{MAX}$. At 76, AV3 is used for a predetermined number (Q) beats, and then at 77 it is determined whether there was V sensing for at least a fraction R of the Q beats. If yes, the routine goes to 73, and AV3 is used as long as there is V sensing. If no, at 78 it is determined whether AV3+$AV_{MAX}$. If no, AV3 is reset to the lesser of (AV3 and AV increment) or $AV_{MAX}$ at 79, and the routine loops back to 76; if yes, the routine exits.

We claim:

1. A dual chamber pacemaker system, said pacemaker having ventricular pacing means for generating ventricular pace pulses for delivery to a patient's ventricle, atrial pacing means for generating atrial pace pulses for delivery to the patient's atrium, atrial sense means for sensing patient atrial contractions, AV means for timing out an AV interval for timing delivery of a ventricular pace pulse following an atrial sense or pace, and test means for determining the relationship between AV intervals and QT intervals, said test means comprising:

varying means for varying said AV interval to predetermined respective values, measuring means for measuring T-waves and obtaining a measure of QT interval corresponding to each respective AV value;

means for determining from said corresponding QT and AV intervals when said AV intervals correspond to capture and when said AV intervals correspond to fusion; and said AV means having AV control means for setting said AV interval as a function of said determining.

2. The pacemaker system as described in claim 1, further comprising selection means for selecting one of a plurality of applications, and wherein said AV control means controls said AV interval as a function of said selected application.

3. The pacemaker system as described in claim 2, wherein said selection means comprises means for selecting a hypertrophic obstructive cardiomyopathy (HOCM) application which controls said AV interval to be just less that corresponding to ventricular fusion.

4. The pacemaker system as described in claim 2, wherein said selection means comprises capture means for enabling selection of an application which controls said AV interval to be of a value which insures full capture upon delivering of a ventricular pace pulse.

5. The pacemaker system as described in claim 1, wherein said varying means comprises means for varying AV interval to each of n predetermined values and maintaining each respective AV interval value for a predetermined number of cycles.

6. The pacemaker system as described in claim 1, further comprising T-wave means for determining when T-waves are not sensed following a delivered ventricular pace pulse.

7. A method in a dual chamber pacemaker system for setting an AV interval value for achieving a selected application, comprising:

varying AV interval over a predetermined range of values;

determining QT intervals that correspond to respective AV intervals in said range;

analyzing said QT and AV intervals and determining therefrom whether said AV intervals correspond to capture or ventricular fusion; and setting said AV interval value as a function of said determining.

8. The method as described in claim 7, comprising determining from said QT and AV intervals a measure of the patient's ventricular fusion zone, and setting said AV interval value as a function of said ventricular fusion zone measure.

9. A dual chamber pacemaker system, having atrial sense means for sensing atrial signals from a patient, ventricular sense means for sensing ventricular signals from a patient, ventricular pace means for generating and delivering ventricular pace pulses to said patient's right ventricle, and sync control means for controlling said pace means to generate and deliver a ventricular pace pulse at a controlled AV escape interval following a sensed atrial signal, said sync control means having $AV_{esc}$ means for setting said AV escape interval, said $AV_{esc}$ means comprising:

QT means for determining data representative of the variation of QT as a function of varying AV escape interval, determining means for determining from said QT data a measure of the ventricular fusion zone, and adjusting means for adjusting said AV escape interval as a function of said ventricular fusion zone measure.

10. The pacemaker system as described in claim 9, comprising application means for storing data representative of a desired pacing application and wherein adjusting means has enabling means for adjusting said AV escape interval in accordance with said application data following a ventricular fusion zone determination.

11. The pacemaker system as described in claim 10, wherein said adjusting means comprises means for determining the QT knee and for setting said AV delay to correspond to a QT value just less than said QT knee.

12. The pacemaker as described in claim 9, comprising means for determining the higher limit of the ventricular fusion zone, so as to maximize the occurrence of natural ventricular heartbeats.

13. The pacemaker as described in claim 9, further comprising hysteresis means for setting a hysteresis value of said AV escape interval as a function of said ventricular fusion zone measure.

* * * * *

UNITED STATES PATENT AND TRADEMARK OFFICE
CERTIFICATE OF CORRECTION

PATENT NO. : 5,713,930

DATED : February 3, 1998

INVENTOR(S) : Johannes S. van der Veen; Geeske van Oort

It is certified that error appears in the above-indentified patent and that said Letters Patent is hereby corrected as shown below:

Col. 1, line 45, "aelpolarization" should read --depolarization--

Col. 8, line 14, "AV13" should read --AV1--

Signed and Sealed this

Fourteenth Day of April, 1998

Attest:

BRUCE LEHMAN

Attesting Officer

Commissioner of Patents and Trademarks